(12) United States Patent
Chiu et al.

(10) Patent No.: US 9,980,919 B2
(45) Date of Patent: May 29, 2018

(54) PREPARATION OF PH-RESPONSIVE NANOPARTICLES AND PROMOTED DELIVERY OF ANTICANCER DRUGS INTO DEEP TUMOR TISSUES AND APPLICATION THEREOF

(71) Applicant: NATIONAL TSING HUA UNIVERSITY, Hsinchu (TW)

(72) Inventors: Hsin-Cheng Chiu, Hsinchu (TW); Wen-Hsuan Chiang, Hsinchu (TW); Chia-Chian Hung, Hsinchu (TW); Ting-Wei Yu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days. days.

(21) Appl. No.: 14/931,872

(22) Filed: Nov. 4, 2015

(65) Prior Publication Data

US 2016/0367489 A1 Dec. 22, 2016

(30) Foreign Application Priority Data

Jun. 22, 2015 (TW) .............................. 104119949 A

(51) Int. Cl.
*A61K 9/51* (2006.01)
*A61K 31/704* (2006.01)
*G01N 33/84* (2006.01)
*A61K 9/00* (2006.01)

(52) U.S. Cl.
CPC .......... *A61K 9/5153* (2013.01); *A61K 9/0019* (2013.01); *A61K 9/5146* (2013.01); *A61K 31/704* (2013.01); *G01N 33/84* (2013.01)

(58) Field of Classification Search
CPC ... A61K 9/5153; A61K 9/5416; A61K 31/704
See application file for complete search history.

(56) References Cited

U.S. PATENT DOCUMENTS

2005/0142182 A1* 6/2005 Wang ................... A61K 9/1272
424/450
2008/0279764 A1* 11/2008 Manganaro .......... A61K 9/0019
424/1.11

FOREIGN PATENT DOCUMENTS

CN 103599069 A 2/2014

OTHER PUBLICATIONS

Zhou et al., International J Pharmaceutics, 487, Jun. 20, 2015, 81-90.*
Zhao et al., Biomaterials, 33, 2508-2520, 2012.*
Zhilan Zhou, et al., "Herception Congated PLGA-PHis-PEG pH Sensitive Nanoparticles for Targeted and Controlled Drug Delievery", International Journal of Pharmaceutics, Jun. 20, 2015, 487 (2015) 81-90.
Xiaolong Tang, et al., Enhanced Antifungal Activity by Ab-Modified Amphotericin B-Loaded Nanoparticles Using a pH responsive Block Copolymer:, Nanoscale Research Letters Dec. 2015; 10(1):969, Epub Jun. 10, 2015.

* cited by examiner

*Primary Examiner* — Kyle A Purdy
(74) *Attorney, Agent, or Firm* — Li&Cai Intellectual Property (USA) Office

(57) ABSTRACT

A pH-responsive nanoparticle made of a pH-responsive polymer and a poly(lactic-co-glycolic acid) by self-assembly includes a polyethylene glycol derivative and a R-Histidine derivative that are subjected to a chemical reaction to form the pH-responsive polymer, wherein the surface electric potential of the pH-responsive nanoparticle is −25 to 10 mV, such that when a pH value of the pH-responsive nanoparticle is changed from 7.4 to 5.0 depending upon an external environment, a surface zeta potential of the pH-responsive nanoparticle is converted from negative charge to positive charge.

10 Claims, 16 Drawing Sheets

US 9,980,919 B2

PREPARATION OF PH-RESPONSIVE NANOPARTICLES AND PROMOTED DELIVERY OF ANTICANCER DRUGS INTO DEEP TUMOR TISSUES AND APPLICATION THEREOF

BACKGROUND OF THE INVENTION

1. Field of the Invention

The instant disclosure relates to an antitumor drug; in particular, to a pH-responsive nanoparticle which can strongly penetrate into tumor tissues.

2. Description of Related Art

The current drugs for curing cancers have significant side effects such as dizziness, hair loss, and skin aging. Hence, researchers have proposed a concept of target therapy. Specifically, target drugs are used to accumulate in tumor tissues through the blood circulation to inhibit the growth of tumor cells. Such called drug controlled release technology has been paid attention to by the medical profession. However, the target drugs existing on the market have many shortcomings that have to be improved. Therefore, the researchers have expended effort to solve the problem of how to decrease the side effects, increase the drug wrapped quantity, and accurately release the drug at the tumor region.

In recent years, polymer micelles have been widely used in medical profession, each of the polymer micelles is composed of amphiphilic polymer chains, wherein one end has hydrophilic chains and the other end has lipophilic chains. The lipophilic chains of the amphiphilic polymer chains would be combined to form a core hydrophobic region in the aqueous phase through the van der Waals force. The core hydrophobic region can be a reservoir for storing lipophilic drugs, and hydrophilic chains are located at the external part of the hydrophobic core to enhance the structural stability of the polymer micelle in the aqueous phase. However, in the highly diluted blood circulation system, the developed polymer micelle still has inferior structural stability and poor accumulation ability for tumor tissues. Thus, the researcher would like to equip a nanocarrier with superior structural stability and effective accumulation ability at the tumor region for the improved delivery of antitumor drugs.

SUMMARY OF THE INVENTION

Target drugs on the current market face some difficult problems in that the drug is wrapped with a low amount of the anticancer drug so that the anticancer drug cannot be accurately accumulated at a tumor area in a large quantity. In order to overcome the above-mentioned problem, this instant disclosure provides a pH-responsive nanoparticle to increase cancer therapy efficacy. The pH-responsive nanoparticles can be accumulated in a tumor acidic environment via the enhanced permeability and retention (EPR) effect to enhance the interaction of the pH-responsive nanoparticle and cancer cells by a surface charge conversion (from negative charge trending to neutral charge), and an ability to permeate into a deep area of the tumor tissues is promoted. In addition, the quantity of the pH-responsive nanoparticles accumulated at the tumor area and the degree of the pH-responsive nanoparticles endocytosed by the cancer cells are both increased, and the anticancer drugs can be delivered into the cancer cells in a large quantity, so as to improve the cancer therapy effect.

In order to achieve the above-mentioned purpose, the instant disclosure provides technical solutions as follows: a pH-responsive nanoparticles are composed of a pH-responsive polymer and a poly(lactic-co-glycolic acid) by self-assembly in an aqueous phase, and characterized in that it includes a polyethylene glycol derivative and a R-Histidine derivative which are subjected to a chemical reaction to form the pH-responsive polymer, wherein the pH-responsive nanoparticle further comprises a hydrophilic shell and a hydrophobic core.

The pH-responsive polymer is formed from the conjugation of the polyethylene glycol derivative and the R-Histidine derivative by being subjected to an esterification.

The polyethylene glycol derivative includes (D-α-tocopheryl polyethylene glycol 1000 succinate, TPGS) or DSPE-PEG.

The R-Histidine derivative is comprised of a group consisting of N-acetyl-Histidine, L-Histidine, D-Histidine, or 3-Methyl-L-histidine.

The hydrophobic core further includes an anticancer drug, a developer, a photothermal agent, a nano-metal particle, or combinations thereof.

In order to further appreciate the characteristics and technical contents of the present invention, references are hereunder made to the detailed descriptions and appended drawings in connection with the instant disclosure. However, the appended drawings are merely shown for exemplary purposes, rather than being used to restrict the scope of the instant disclosure.

DETAILED DESCRIPTION OF THE PREFERRED EMBODIMENTS

This instant disclosure provides a pH-responsive nanoparticle to be accumulated in a tumor acidic environment via an enhanced permeability and retention (EPR) effect to enhance an interaction force of the pH-responsive nanoparticle and cancer cells (cell membrane being negative charge) by a surface electric potential conversion (from negative charge trending to neutral charge). An ability to permeate into a deep area of tumor tissues is promoted, so as to improve an efficiency of anticancer drugs being endocytosed by the cancer cells and improve an effect of cancer therapy. The instant disclosure does not need to utilize complex processes and excessive organic solvents, and the electric potential conversion process does not involve molecules being separated and hydrolyzed, thus no side products are produced.

Embodiments of the pH-responsive nanoparticle disclosed in the present invention are illustrated via specific examples as follows. The present invention may be implemented or applied by other different specific examples, and each of the details in the specification may be applied based on different views and may be modified and changed keeping the spirit of the present invention. The figures in the present invention are only for brief description, but they are not depicted according to actual size and do not reflect the actual size of the relevant configuration. The following embodiments further illustrate related technologies of the present invention in detail, but the scope of the present invention is not limited herein.

The instant disclosure provides a pH-responsive nanoparticle which is made of a pH-responsive polymer and a poly(lactic-co-glycolic acid), wherein the pH-responsive polymer is made of a polyethylene glycol derivative and a R-Histidine derivative. The polyethylene glycol derivative is comprised of a group consisting of a D-α-tocopheryl polyethylene glycol 1000 succinate (TPGS), or 1,2-distearoyl-sn-glycero-3-phosphoethanolamine-N-maleimide(polyethylene glycol) (DSPE-PEG). The R-Histidine derivative is comprised of a group consisting of N-acetyl-Histidine, L-Histidine, D-Histidine, or 3-Methyl-L-histidine.

First Embodiment

Figure 1:
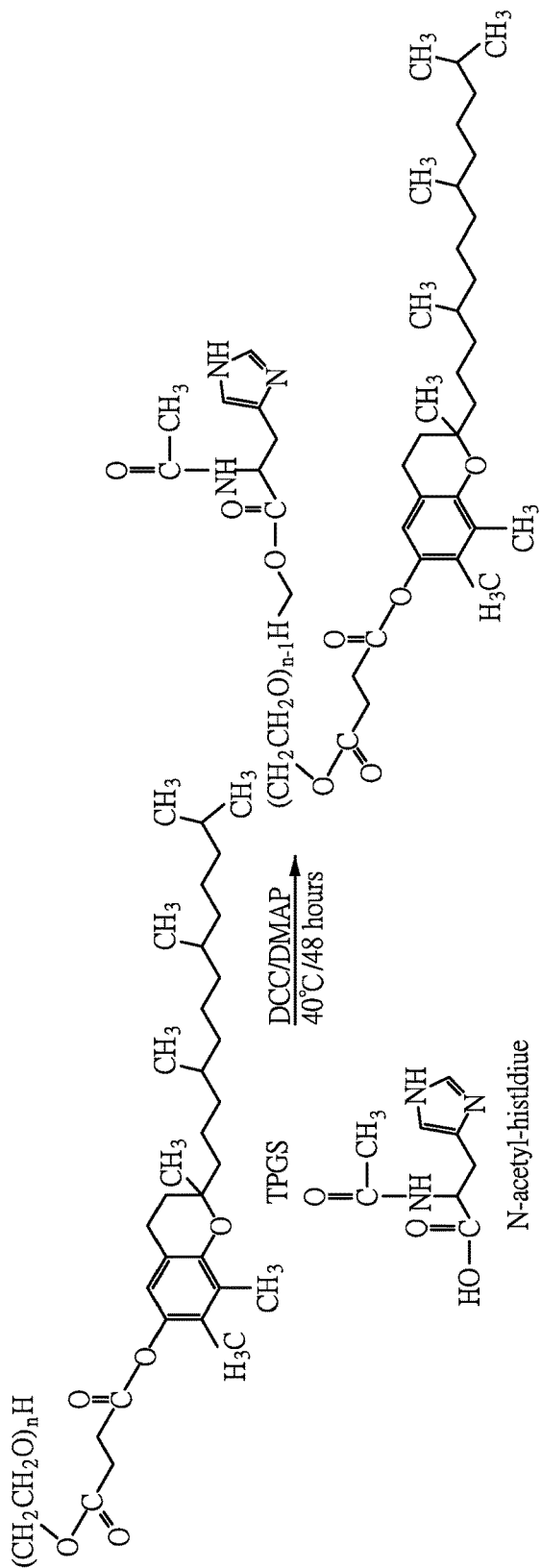
FIG. 1 shows a schematic view of synthesis of a NAcHis-TPGS of an embodiment in the instant disclosure.
Figure 2:
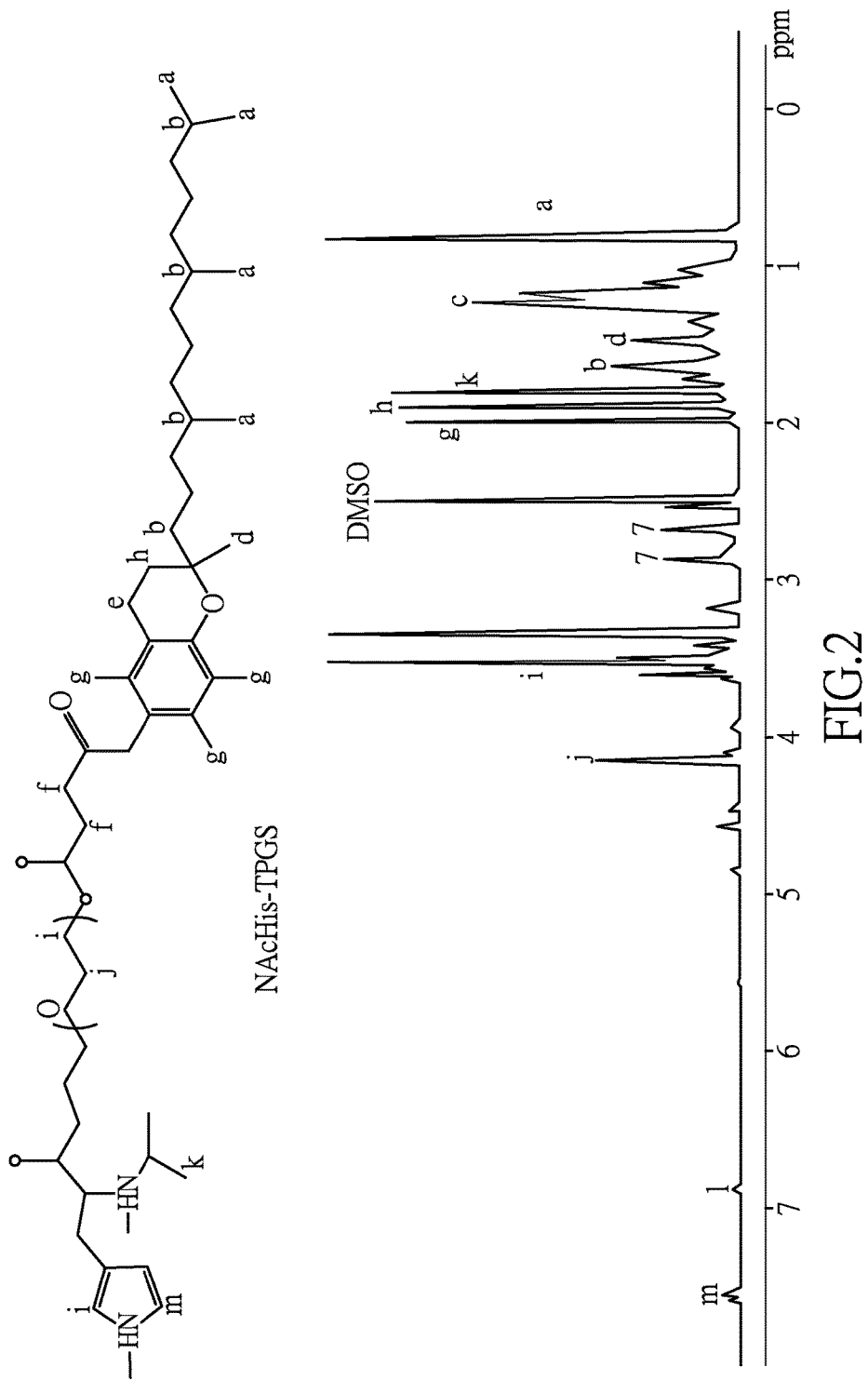
FIG. 2 shows an $^1$H-NMR spectrum of the NAcHis-TPGS of an embodiment in the instant disclosure.

Please refer to FIGS. 1 and 2. The pH-responsive nanoparticle of an embodiment in the instant disclosure was formed by using the N-Acetyl Histidine to modify the TPGS to synthesis a compound called NAcHis-TPGS. In the embodiment, the synthesis method was Steglich esterification, and the specific steps are as follows:

The TPGS (3 g, 2.0 mmol), N-acetyl-1-histidine (1.97 g, 10.0 mmol), N,N'-dicyclohexylcarbodiimide (DCC) (1.24 g, 6.0 mmol), and a bit of 4-Dimethylaminopyridine (DMAP) (0.24 g, 2.0 mmol) were dissolved in an anhydrous Dimethyl sulfoxide (DMSO) (10.0 mL), followed by stirring the above mixed solution for 48 hours at 40° C. The ideal condition was that the N-acetyl-1-histidine was added in an amount of 5 times the molar number of the TPGS, and the DCC was added in an amount of 3 times the molar number of the TPGS.

Dicyclohexylcarbodiurea (DCU) generated from the abovementioned experimental process and the DMSO was removed. In the embodiment, the DCU was removed by repeated suction filtration, and a product (golden yellow liquid) was placed in a dialysis bag (MWCO 1000). The NAcHis, DMAP, and DMSO was dialyzed, the process lasting 7 days at room temperature, in order to remove residual reactants that were not synthesized completely in the solution, and deionized water was dialyzed, the process lasting 7 days, to remove the DMSO in the solution.

The abovementioned solution was frozen and dried to obtain a synthesized compound of N-acetyl-1-histidine modified TPGS, called NAcHis-TPGS.

FIG. 2 shows a $^1$H-NMR spectrum of the NAcHis-TPGS of the embodiment in the instant disclosure. The NAcHis-TPGS was purified and dissolved in a DMSO-d6 solvent, a nuclear magnetic resonance ($^1$H-NMR) spectroscopy at 500 MHz was used for quantitative analysis of the polymer composition, a methyl group (peak a) at a terminal end of the TPGS having a chemical shift of the proton peak was 0.81 ppm, a C-4 carbon of an imidazole group (peak m) of the N-Acetyl-Histidine having a chemical shift was 7.55 ppm, an integrated area ratio of the peak a and the peak m was calculated to compare with total number of hydrogen of the theoretical unit, and an efficiency of the N-Acetyl-Histidine being bound to the TPGS was obtained. After calculation, the terminal end group of the TPGS having a modified rate was about 94.7%, and its yield was 88.0%.

Figure 3:
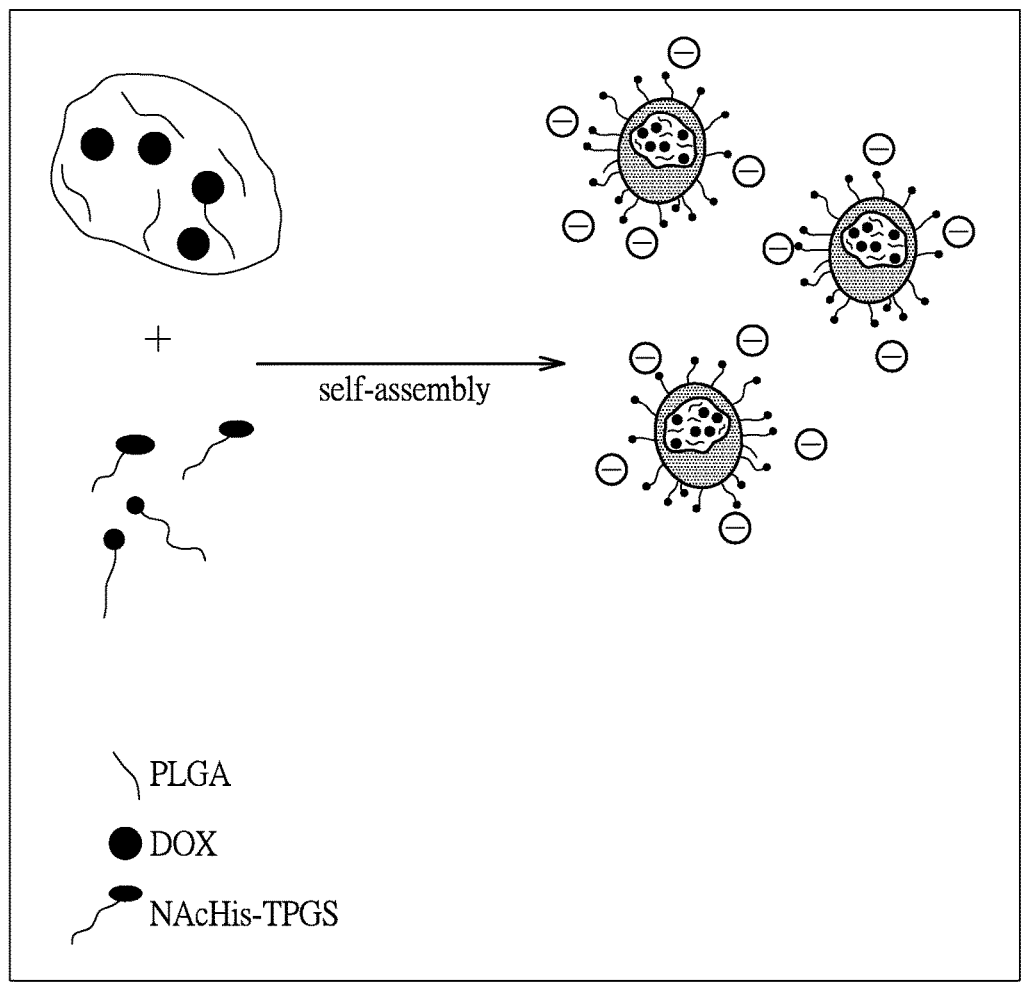
FIG. 3 shows a schematic view of preparation of a pH-responsive nanoparticle DOX-loaded NHTPNs of an embodiment in the instant disclosure.
Figure 4:
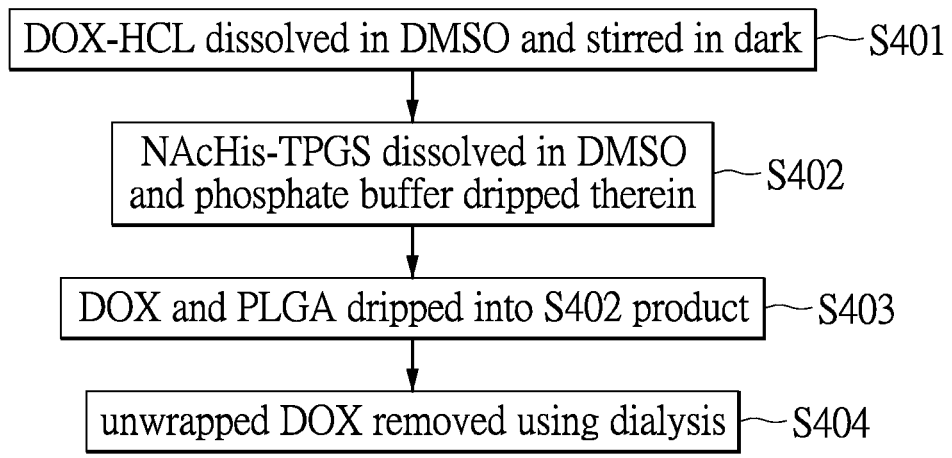
FIG. 4 shows preparation steps of the pH-responsive nanoparticle DOX-loaded NHTPNs of an embodiment in the instant disclosure.

Please refer to FIGS. 3 and 4. FIG. 3 shows a schematic view of preparation of a pH-responsive nanoparticle DOX-loaded NHTPNs of the embodiment in the instant disclosure, and FIG. 4 shows preparation steps of the pH-responsive nanoparticle DOX-loaded NHTPNs of the embodiment in the instant disclosure.

In step S401, DOX.HCl was dissolved in DMSO and excess triethylamine (1.5-fold excess in molar concentration with respect to DOX) was added therein to stir for 48 hours at room temperature in the dark, and the purpose was to increase a hydrophobicity of the DOX, so as to improve a drug loading efficiency. In the instant disclosure, the instant disclosure is not limited to the type of the anticancer drugs.

In step S402, the premodified NAcHis-TPGS was dissolved in DMSO (0.05 mL) and then added dropwise dripped into 0.01 M phosphate buffer (pH 7.4, 3.5 mL) under vigorous stirring for 5 minutes with rotating speed of 1350 rpm. The ideal condition was that the NAcHis-TPGS was added in an amount of 80 wt % of the PLGA.

In step S403, during stirring, the PLGA(LA/GA=85/15 mol ratio) predissolved in DMSO (0.45 mL) and DOX were slowly added dripped into the product obtained from step S402. After that, the above solution was then vigorously stirred for 30 minutes at 30° C. The ideal condition was that the DOX was added in an amount of 20 wt % of the PLGA.

In step S404, the above evenly mixed solution was stood for 30 minutes at room temperature and was then poured into the dialysis bag (MWCO 12000 to 14000), and was dialyzed against the 0.01 M phosphate buffer (pH 7.4) for one day at 4° C. to remove the unloaded DOX and the DMSO solvent, then the dialyzed pH-responsive nanoparticle DOX-loaded NHTPNs solution was stored in a 4° C. refrigerator for subsequent experiments.

As shown in FIG. 3, the pH-responsive nanoparticle DOX-loaded NHTPNs being formed by self-assembly in the aqueous phase were nanoscale particles, wherein the pH-responsive amphiphilic polymer NAcHis-TPGS having a PEG hydrophilic end was located at an external part of a drug-containing hydrophobic core (made of DOX carried PLGA).

For comparison, DOX-loaded TPGS/PLGA Nanoparticles (DOX-loaded TPNs) and drug free nanoparticles (NHTPNs) were respectively prepared via an identical process to be an experimental control group.

Figure 5:
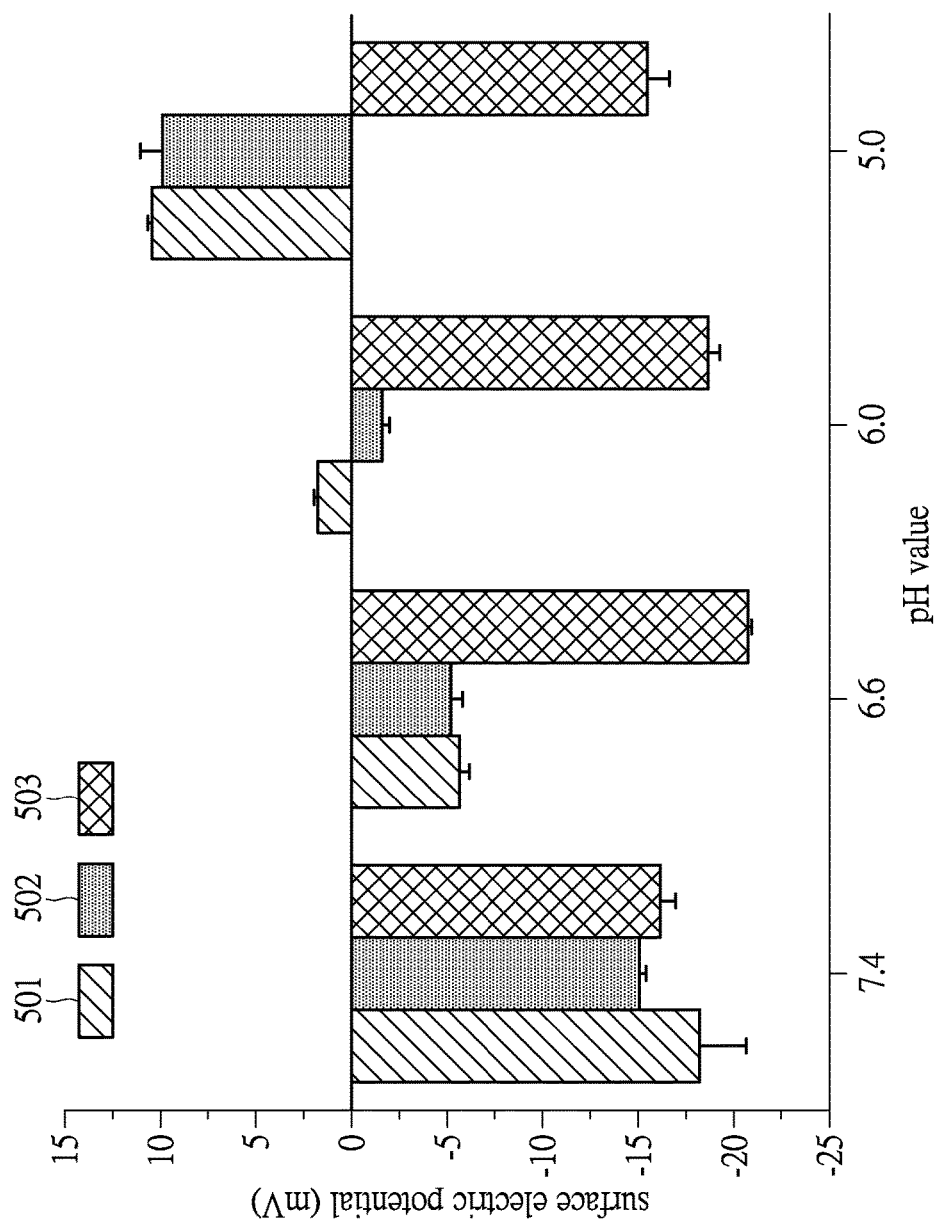
FIG. 5 shows an interface electric potential chart of the pH-responsive nanoparticle DOX-loaded NHTPNs and a control group of an embodiment in the instant disclosure.

FIG. 5 shows an interface electric potential chart of the pH-responsive nanoparticle DOX-loaded NHTPNs and a control group of the embodiment in the instant disclosure. The interface electric potential chart shows that, even if histidine groups of surfaces of a test group DOX-loaded NHTPNs 502 and a test group NHTPNs 501 are substantially protonated in a weak acidic aqueous phase, an electrical property on the surface of the particles are able to convert from negative charge to positive charge. In contrast, a test group DOX-loaded TPNs 503 has no an electric potential conversion property. In addition, when pH is decreased from 6.6 to 6.0, the test group DOX-loaded NHTPNs 502 tends to generate aggregation between particles during the electric potential conversion, so as to facilitate increasing an accumulation degree of the pH-responsive nanoparticle DOX-loaded NHTPNs in living tumors and the release of the anticancer drug to kill cancer cells.

Figure 6:
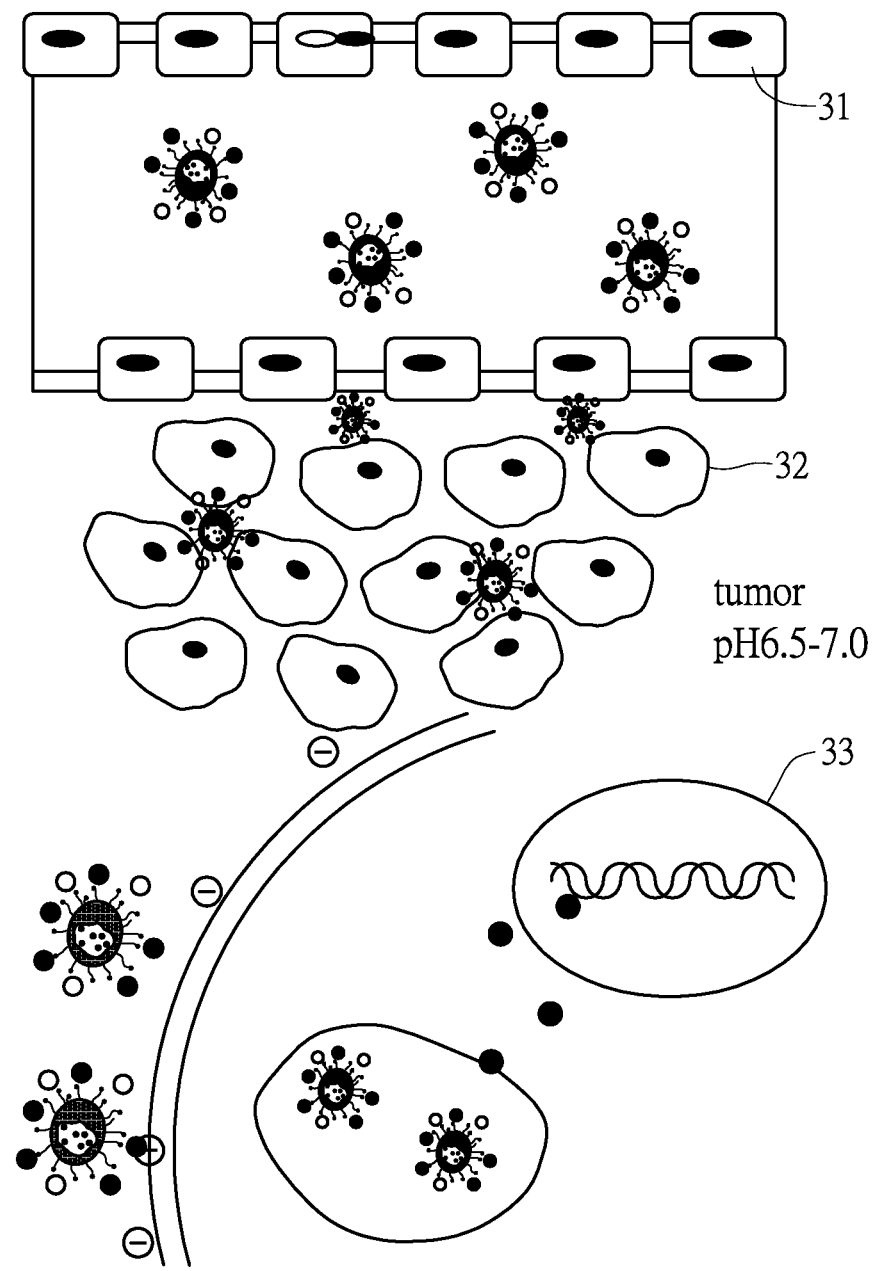
FIG. 6 is a drug delivery system of the pH-responsive nanoparticle DOX-loaded NHTPNs of an embodiment in the instant disclosure.

FIG. 6 is a drug delivery system 30 of the pH-responsive nanoparticle DOX-loaded NHTPNs of an embodiment in the instant disclosure. As shown in FIG. 6, the pH-responsive nanoparticle DOX-loaded NHTPNs do not penetrate into normal cells 31. In contrast, an external PLGA core bonded NAcHis-TPGS can be substantially protonated to increase positive charge on the surface of the particles via the imidazole functional group on the histidine group in the acidic environment of the tumor tissue, so as to facilitate the accumulation of the pH-responsive nanoparticle DOX-loaded NHTPNs in the weak acidic environment of the tumor region through the EPR effect. When the surface electricity of the pH-responsive nanoparticle DOX-loaded NHTPNs is converted from negative charge to positive charge, the endocytosis efficiency of the pH-responsive nanoparticle DOX-loaded NHTPNs by the tumor cells is improved, such that the anticancer drug DOX would be delivered into the nucleus 33 of the tumor cell 32 to enhance the effect of killing cancer cells.

Figure 7:
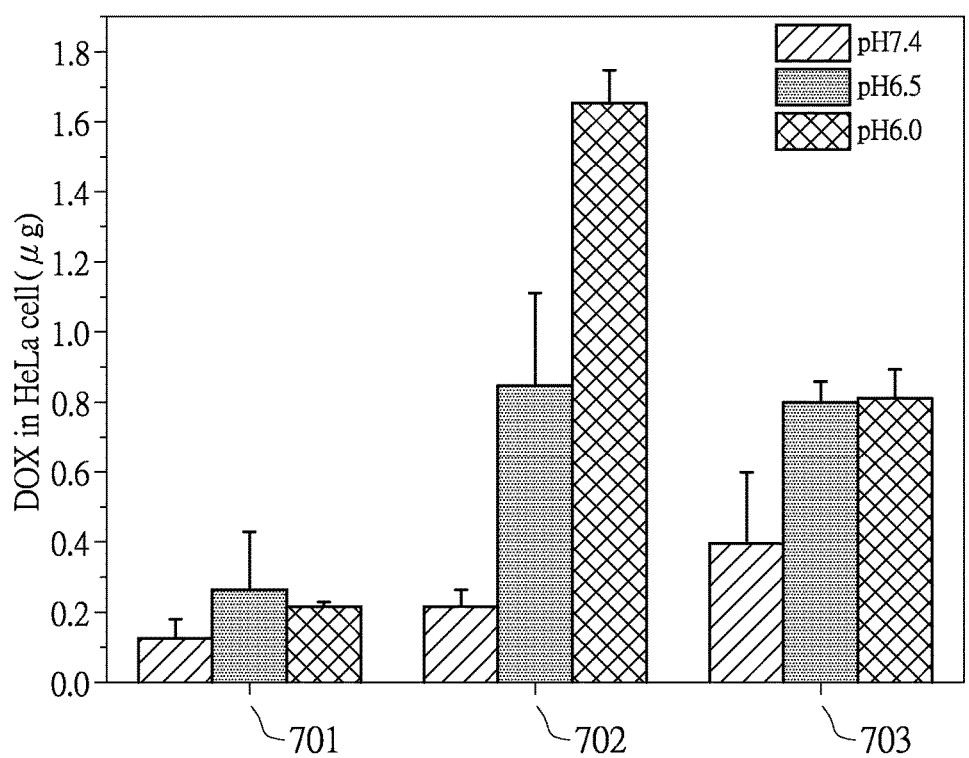
FIG. 7 shows a DOX concentrations chart in HeLa cell of the pH-responsive nanoparticle DOX-loaded NHTPNs and the control group of an embodiment in the instant disclosure.

FIG. 7 shows a DOX concentration chart in HeLa cells of the pH-responsive nanoparticle DOX-loaded NHTPNs and the control group of the embodiment in the instant disclosure. HeLa cells and the pH-responsive nanoparticle DOX-loaded NHTPNs were co-cultured two hours in a weak acidic environment (pH 6.5, pH 6.0) and normal culturing environment (pH 7.4) respectively, an intracellular drug concentration was measured using an ELISA reader, and the analyzed results showed that a test group DOX-loaded NHTPNs 702 could sharply increase an in-taken amount by the cancer cells in the weak acidic state. Therefore, the intracellular DOX concentration was significantly elevated.

In comparison with the normal culturing condition (pH 7.4), the intracellular drug accumulation quantity of the pH-responsive DOX-loaded NHTPNs of the instant disclosure can be increased at least 4 times in the weak acidic environment (pH 6.0). In a test group of DOX-loaded TPNs 703 in a different pH environment, the DOX concentration in the HeLa cells has no significant change. In a test group of Free DOX 701 in a different pH environment, the DOX concentration in the HeLa cells also had no significant change. The above experimental results show that, the NAcHis-TPGS coated on the surface of the pH-responsive nanoparticle DOX-loaded NHTPNs can provide a function of charge conversion on the surface of the pH-responsive nanoparticle, and can further promote the endocytosis efficiency of the pH-responsive nanoparticle DOX-loaded NHTPNs by the cancer cells in the weak acidic environment.

Second Embodiment

Figure 8:
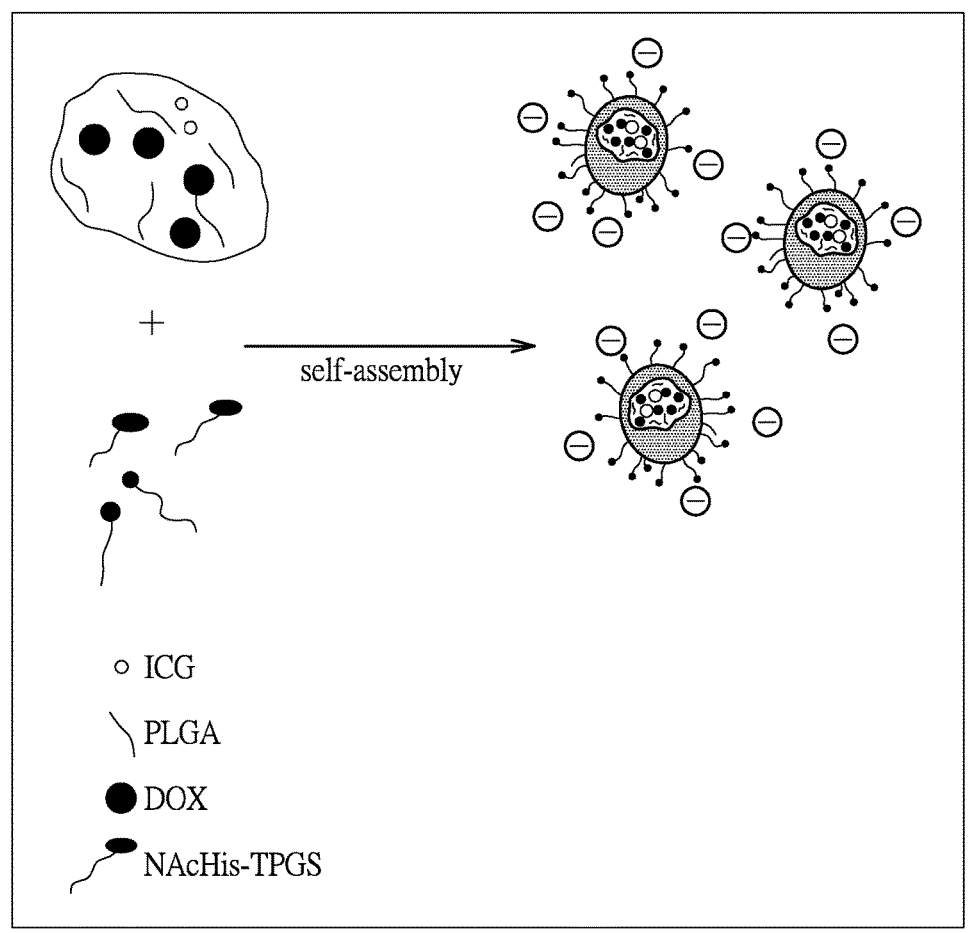
FIG. 8 shows a schematic view of preparation of a pH-responsive nanoparticle ICG/DOX-loaded NHTPNs of an embodiment in the instant disclosure.
Figure 9:
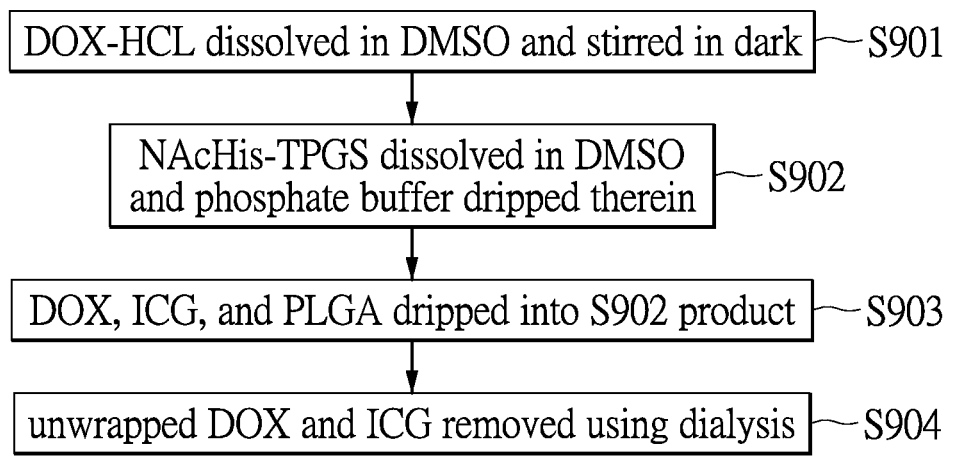
FIG. 9 shows preparation steps of the pH-responsive nanoparticle ICG/DOX-loaded NHTPNs of an embodiment in the instant disclosure.

Please refer to FIGS. 8 and 9. FIG. 8 shows a schematic view of a preparation of pH-responsive nanoparticle ICG/DOX-loaded NHTPNs of an embodiment in the instant disclosure, and FIG. 9 shows preparation steps of the pH-responsive nanoparticle ICG/DOX-loaded NHTPNs of an embodiment in the instant disclosure.

In step S901, DOX.HCl was dissolved in the DMSO and excess triethylamine (1.5-fold excess in molar concentration with respect to DOX) was added therein to stir for 24 hours at room temperature in the dark, and the purpose was to increase the hydrophobicity of the DOX, so as to improve the drug loading efficiency.

In step S902, a DMSO (0.05 mL) solution containing NAcHis-TPGS (1.6 mg) was slowly dripped into a 0.01 M phosphate buffer (pH 7.4) under stirring with a magnet, and was then stirred for 5 minutes with a rotating speed of 1350 rpm. The ideal condition was that a 0.05 mL DMSO solution containing 1.8 mg NAcHis-TPGS (feed amount is 80 wt % of the PLGA) was slowly dripped into 2.8 mL of phosphate buffer under stirring with the magnet.

In step S903, during stirring, a DMSO solution containing PLGA (LA/GA=85/15 mol ratio), DOX, and a photothermal agent indocyanine green (ICG) was slowly dripped into the phosphate buffer containing NAcHis-TPGS solution (DMSO/Water (v/v)=1/7) to stir for 30 minutes at 30° C. with the magnet. The ideal condition was that, the 350 μL DMSO solution contains 2 mg PLGA, 0.4 mg DOX, and 0.4 mg ICG therein.

In step S904, the product obtained from step S903 was put into the dialysis bag (MWCO 12000 to 14000) and was dialyzed against the phosphate buffer for 24 hours to remove the unloaded drugs and DMSO, so as to obtained a pH-responsive nanoparticle ICG/DOX-loaded NAcHis-TPGS/PLGA Nanoparticles (Abbreviated called ICG/DOX-loaded NHTPNs) solution. After the ICG/DOX-loaded NHTPNs were dialyzed, the ICG/DOX-loaded NHTPNs were stored in a 4° C. refrigerator for subsequent experiments.

For comparison, ICG/DOX-loaded TPGS/PLGA Nanoparticles (ICG/DOX-loaded TPNs), ICG-loaded NHTPNs, and drug free nanoparticles (NHTPNs) were respectively prepared via an identical process to be an experimental control group.

Figure 10:
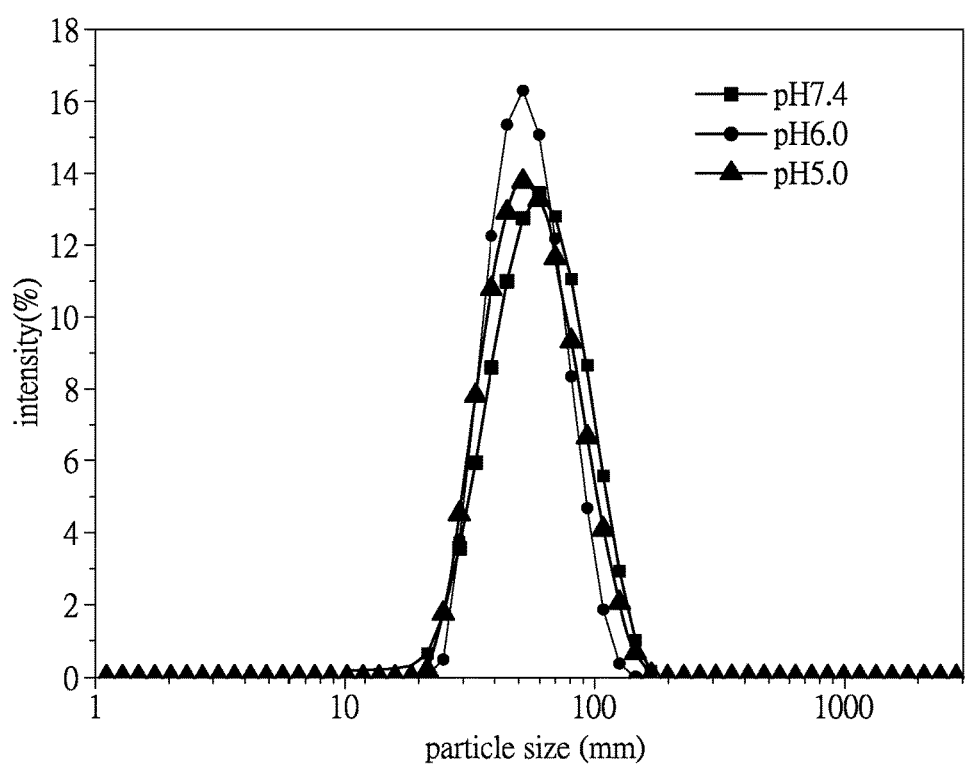
FIG. 10 shows a figure of particle sizes distribution of the pH-responsive nanoparticle ICG/DOX-loaded NHTPNs of an embodiment in the instant disclosure.

FIG. 10 shows a figure of a particle size distribution of the pH-responsive nanoparticle ICG/DOX-loaded NHTPNs of an embodiment in the instant disclosure. With the decrease of pH value from pH 7.4 to pH 5, no a significant variation in the particle size was observed. The particle size distribution figure shows that the pH-responsive ICG/DOX-loaded NHTPNs maintain about 50 nm of particle size, and shows the particle's superior physical stability. Relying upon the pH-responsive nanoparticle ICG/DOX-loaded NHTPNs of the instant disclosure having smaller particle size and a near neutral surface in the weak acidic aqueous phase, the pH-responsive nanoparticle ICG/DOX-loaded NHTPNs have long residence time in the blood circulation. Meanwhile, their permeability of tumor tissues and ability to be internalized by cancer cells are enhanced, so as to significantly increase the drug concentration in the cancer cells.

Figure 11:
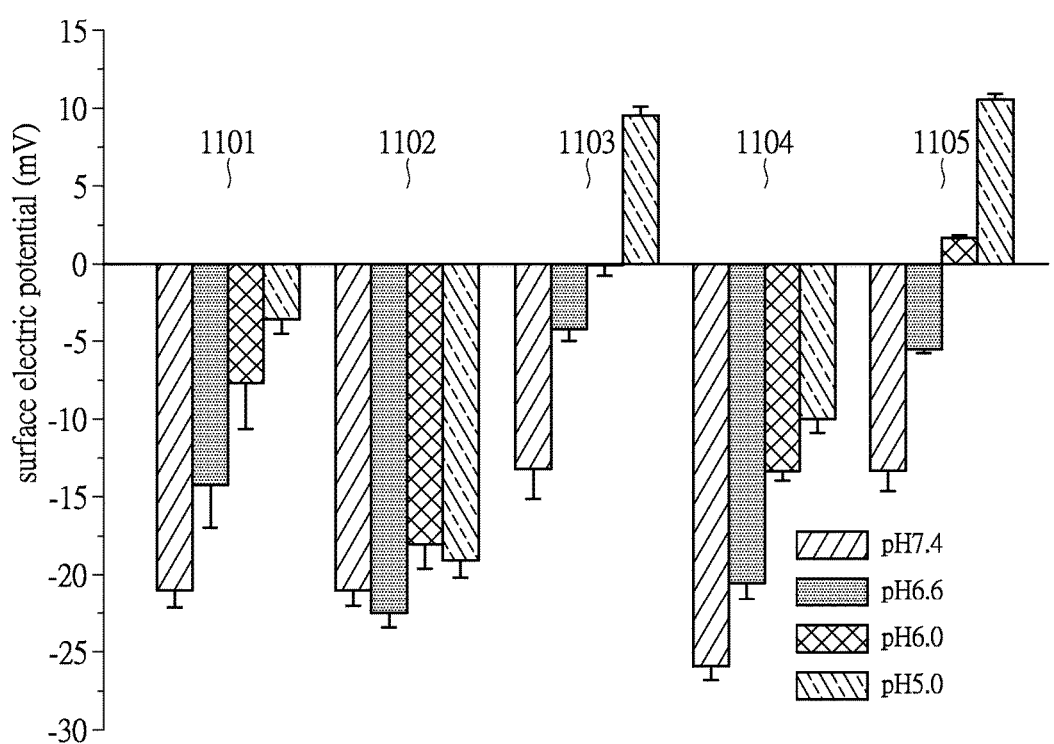
FIG. 11 shows an interface electric potential chart of the pH-responsive nanoparticle ICG/DOX-loaded NHTPNs and a control group of an embodiment in the instant disclosure.

FIG. 11 shows an interface electric potential chart of the pH-responsive nanoparticle ICG/DOX-loaded NHTPNs and a control group of the embodiment in the instant disclosure. In FIG. 11, each of the control groups are test group ICG/DOX-loaded NHTPNs 1101, test group ICG/DOX-loaded TPNs 1102, test group DOX-loaded NHTPNs 1103, test group ICG-loaded NHTPNs 1104, and test group NHTPNs 1105.

When the pH was decreased from 7.4 to 5.0, the results of the test group ICG/DOX-loaded NHTPNs 1101, test group DOX-loaded NHTPNs 1103, test group ICG-loaded NHTPNs 1104, and test group NHTPNs 1105 show that their surface zeta potential tend to change from negative to neutral or positive value. That is to say, the surface positive charges of the nanoparticles are appreciably increased in the weak acidic tumor, thus facilitating their tumor accumulation and cellular uptake by the cancer cells. The test group ICG/DOX-loaded TPNs 1102 does not have the pH-responsive property due to the lack of the NAcHis on the particle surface.

This interface zeta potential conversion phenomenon is due to the fact that, when the pH-responsive nanoparticle is in the neutral environment (pH 7.4), the surface adsorbs anions from the aqueous phase and has slightly negative charge. However, when the surrounding environment becomes weak acid, hydrogen ions in the aqueous phase will cause a sharp increase of the positive charge on the surface of the pH-responsive nanoparticle owing to the significantly increased protonation of imidazole functional group of the histidine residues on the surface of the pH-responsive nanoparticles.

Such obvious charge conversion effect prevents the removal of pH-responsive nanoparticles by immune cells in the blood circulation (pH 7.4) by decreasing the non-specific adsorption of serum protein to the particles. In addition, when the pH-responsive nanoparticles enter into the weak acidic tumor environment, the degree of pH-responsive nanoparticle engulfed by cancer cells is increased upon increase of the electrostatic attraction between the positively charged particles and the cell membrane having negative charge. Furthermore, since the ICG molecule has two sulfonate groups (pKa is about 2.0), the test group ICG-loaded NHTPNs 1104 has negative charge at a range of pH 5.0 to 7.4. When the ICG and NAcHis-TPGS are co-embedded to the surface of the hydrophobic PLGA core, the ability of charge conversion of the ICG-loaded nanoparticles is lowered to some extent. Nevertheless, the test group ICG/DOX-loaded NHTPNs 1101 and the test group ICG-loaded NHTPNs 1104 still can retain charge conversion ability in the weak acidic environment (pH 6.0) and near neutral surface, a critical prerequisite for the infiltration into deep tumor tissue in vivo.

Figure 12:
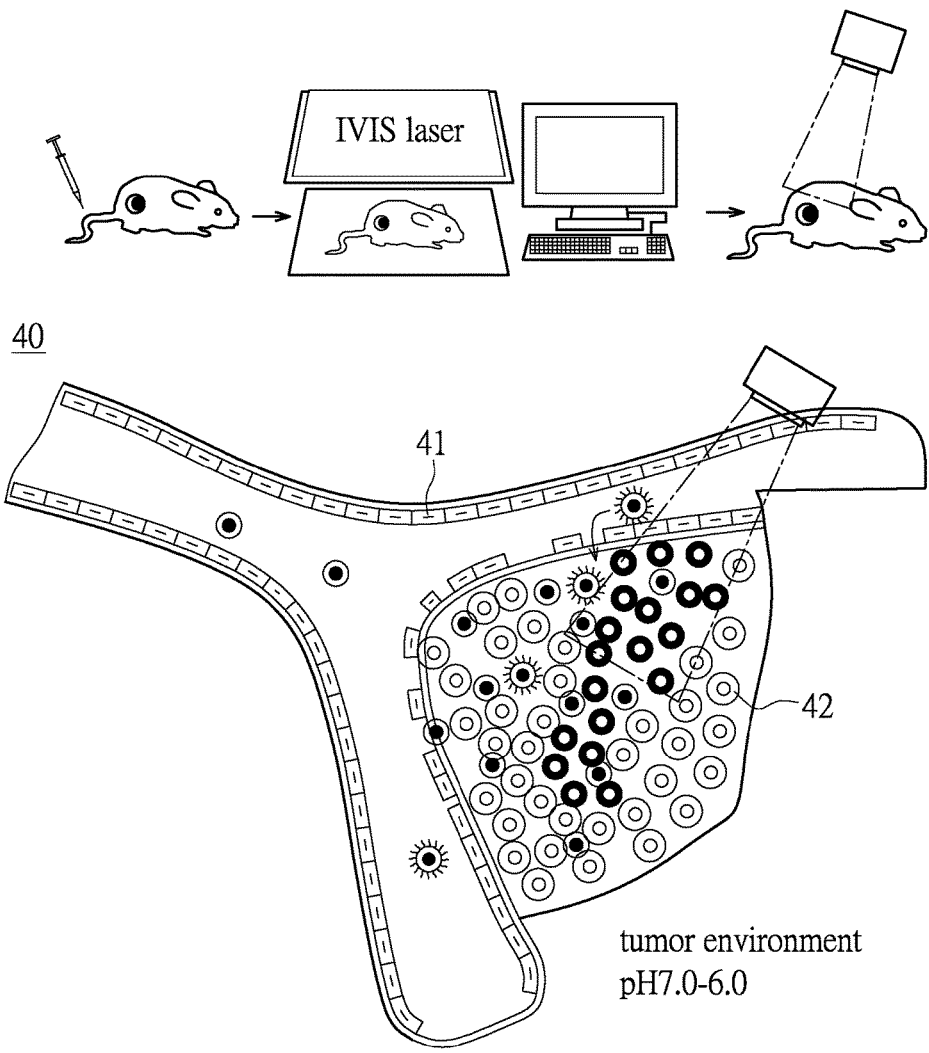
FIG. 12 is a drug delivery system of the pH-responsive nanoparticle ICG/DOX-loaded NHTPNs of an embodiment in the instant disclosure.

FIG. 12 is a drug delivery system 40 of the pH-responsive nanoparticle ICG/DOX-loaded NHTPNs of an embodiment in the instant disclosure. The free ICG, free DOX, ICG/DOX-loaded NHTPNs, and TPNs were dispersed in DMEM (Dulbecco's modified Eagle medium) of different pH values (7.4, 6.6, and 6.3) to an ICG or DOX concentration of 20 □M. The mouse prostate cancer cells (TRAMP-C1) seeded at a density of $3\times10^5$ cells per well in 12-well culture plates were incubated with the above solutions at 37° C. for 2 hours and then washed three times with PBS. DMSO (0.65 mL) was added for cell disruption. The collection of fluorescence signals of ICG (Ex. 745 nm and Em. 810 nm) was conducted on an IVIS (Xenogen IVIS Spectrum). The amount of DOX uptaken by TRAMP-C1 cells was determined by fluorescence measurements. The absorbance of ICG at 775 nm and the DOX fluorescence in the range 500 to 700 nm were determined, respectively, by a UV/Vis spectrophotometer and a fluorescence spectrometer. When the pH-responsive nanoparticle ICG/DOX-loaded NHTPNs are in the weak acidic tumor environment (pH 7.0 to 6.0), the degree of the pH-responsive nanoparticle ICG/DOX-loaded NHTPNs endocytosed by tumor cells 42 is improved, since there is an increase of partly protonated histidine units on the surface and electrostatic interaction force of the tumor cells. Due to the particle size of the pH-responsive nanoparticle ICG/DOX-loaded NHTPNs being small and its surface having almost neutral electricity, not only can the degree of endocytosis by the tumor cells 42 be improved, but also the opportunity of endocytosis by tumor related macrophages can be elevated, and the pH-responsive nanoparticle ICG/DOX-loaded NHTPNs arrive at an anoxic zone to further kill the tumor cells 42.

Figure 13:
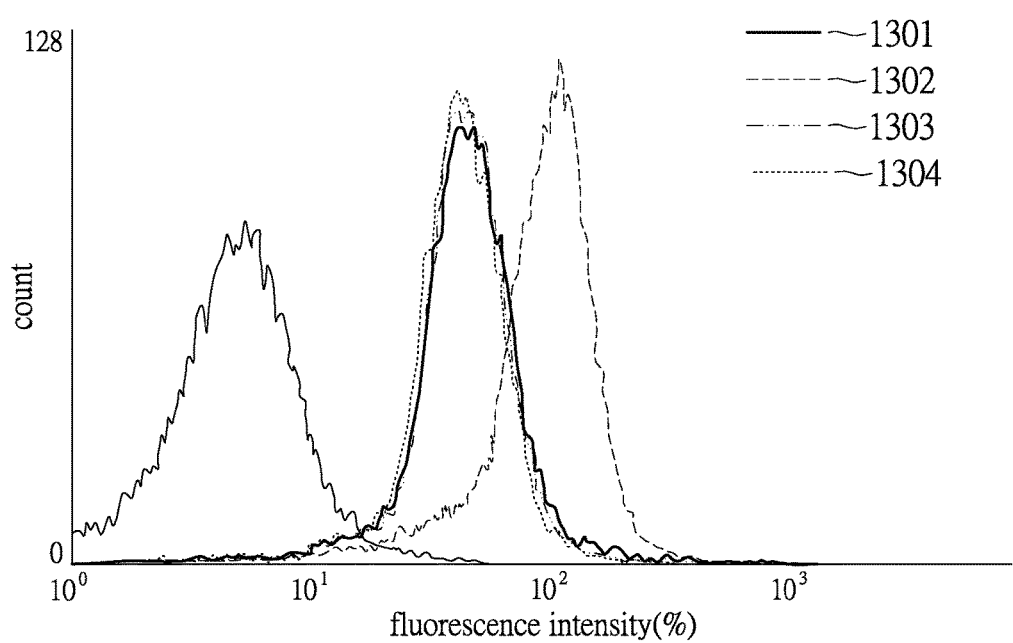
FIG. 13 shows a flow cytometry analysis chart of DOXs detected in TRAMP-C1 cells of the pH-responsive nanoparticle ICG/DOX-loaded NHTPNs of an embodiment in the instant disclosure.

FIG. 13 shows a flow cytometry analysis chart of DOXs detected in TRAMP-C1 cells of the pH-responsive nanoparticle ICG/DOX-loaded NHTPNs of an embodiment in the instant disclosure. The FACSCalibur flow cytometer was utilized to assess cellular uptake of ICG/DOX-loaded NHTPNs and TPNs (DOX concentration=20 □M) by TRAMP-C1 cells at 37° C. and at pH 7.4 and 6.3. After 2 hours incubation, the treated TRAMP-C1 cells ($3\times10^5$ cells/well) were detached with trypsine-EDTA solution and then suspended in PBS (1.0 mL), giving a cell suspension containing a minimum of $1\times10^4$ cells. Additionally, the flow cytometry analysis results show that, the TRAMP-C1 cells are co-cultured with a test group ICG/DOX-loaded NHTPNs at pH 6.3 1302, the fluorescence intensity of DOX of the cells in the weak acidic environment is significantly higher than the TRAMP-C1 cells being co-cultured with a test group ICG/DOX-loaded NHTPNs at pH 7.4 1301, and is significantly higher than the groups without wrapping the NAcHis on the surface of nanoparticles, that is a test group ICG/DOX-loaded TPNs at pH 7.4 1303 and a test group ICG/DOX-loaded TPNs at pH 6.3 1304. Therefore, the nanoparticles with NAcHis-TPGS wrapped on the surface can indeed provide the function for pH-responsive charge conversion on the surface, and can further improve the efficiency of pH-responsive nanoparticle ICG/DOX-loaded NHTPNs endocytosed by cancer cells in the weak acidic environment.

Figure 14:
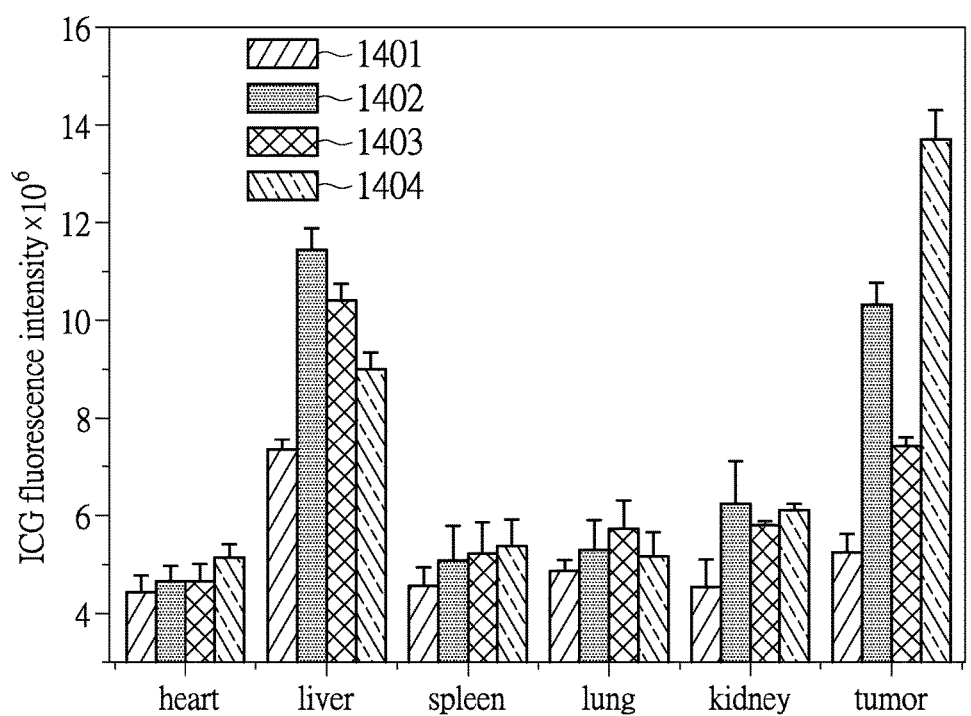
FIG. 14 shows a proportional chart of ICGs accumulated in each organs of a mouse of the pH-responsive nanoparticle ICG/DOX-loaded NHTPNs of an embodiment in the instant disclosure.

Please refer to FIGS. 12 and 14. FIG. 14 shows a proportional chart of ICGs accumulated in each of the organs of a mouse treated with the pH-responsive ICG/DOX-loaded NHTPNs of the embodiment in the instant disclosure. Male C57BL/6J mice (6-8 weeks old) purchased from National Laboratory Animal Center (Taiwan), were cared in accordance with the Guidance Suggestions for the Care and Use of Laboratory Animals, approved by the Administrative Committee on Animal Research in the National Tsing Hua University (Taiwan). To establish tumor model, $2\times10^7$ TRAMP-C1 cells were subcutaneously injected into the right thigh of mice. Two weeks post-inoculation, the low permeability tumor model was established. Tumor volume (V) was calculated as follows: V=L× $W^2$/2, where W is the tumor measurement at the widest point and L the tumor dimension at the longest point. When the tumor volume reached 100 to 120 mm$^3$, PBS, free ICG, or various nanoformulations were injected into the mice via tail vein at an ICG dosage of 1.6 mg/kg. The fluorescence signals of ICG (Ex. 745 nm and Em. 810 nm) at 2, 4, 6, 24 and 48 h post-injection were collected on the IVIS. The treated mice were then sacrificed and the major organs harvested for individual organ imaging by IVIS. After tail vein injection for 48 hours and observation in vivo experiments, the mouse was sacrificed and its major organs and tumors taken for detecting ICG fluorescent performance of each organ using a non-invasive in vivo imaging system (IVIS). A test group Free ICG 1401 had no fluorescent expression in the tumor, the fluorescence mostly expressed in the liver, and the results are in keeping with most literature reports having reported that the liver is the major metabolic organ for ICG.

It is worth mentioning that, the pH-responsive ICG/DOX-loaded NHTPNs groups showing the fluorescence intensity accumulating in the tumor is significantly higher than that in the liver, the fluorescence intensity of the test group ICG/DOX-loaded NHTPNs 1404 in the tumor is significantly higher than the test group Free ICG 1401, the test group ICG-loaded NHTPNs 1402, and the test group ICG/DOX-loaded TPNs in the tumor. Accordingly, the pH-responsive ICG/DOX-loaded NHTPNs having the ability of surface charge conversion in the weak acidic tumor environment can avoid the ICG being quickly metabolized by liver and can effectively promote the ICG being accumulated in the tumor, so as to provide good tumor imaging and subsequent photothermal therapy to further inhibit the tumor growth.

Figure 15:
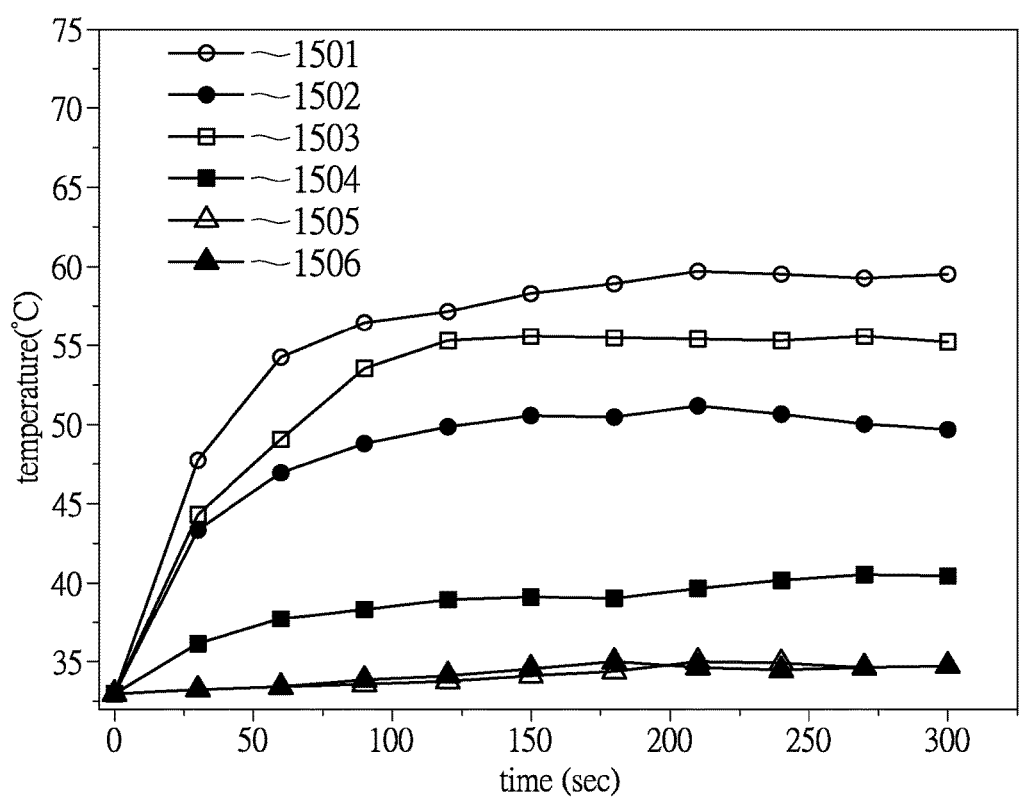
FIG. 15 is a time—temperature figure of the pH-responsive nanoparticle ICG/DOX-loaded NHTPNs of an embodiment in the instant disclosure.

Please refer to FIG. 15. FIG. 15 is a time—temperature figure of the pH-responsive ICG/DOX-loaded NHTPNs of an embodiment in the instant disclosure. When tumor volume of the mice reached 100 to 120 mm$^3$, the mice were randomly divided into six groups (10 in each group) and separately treated by I.V. injection with PBS, free ICG, free DOX, ICG-loaded NHTPNs, ICG/DOX-loaded NHTPNs, and TPNs at an ICG dosage of 1.6 mg/kg or, in the case of free DOX, 1.8 mg/kg. 6 hours post-injection, the mice (5 in each group) were irradiated at the tumor sites with 808 nm laser (1.0 W/cm$^2$) for 5 min. The tumor volumes of various groups were measured daily and normalized against the original volumes to assess the antitumor efficacy. The tumor local temperature was monitored by infrared thermal imaging camera. A test group ICG/DOX-loaded NHTPNs 1501, test group ICG/DOX-loaded TPNs 1503, and test group ICG/DOX-loaded TPNs 1502 were evaluated along with temperature changes over time, while a test group PBS 1506, a test group Free ICG 1504, and a test group Free DOX 1505 were the experimental control groups. After the tumors were irradiated by an NIR laser, since the test group PBS 1506 and the test group Free DOX 1505 lacked a photothermal conversion characteristic, the temperature of the tumors was not significantly elevated.

It is worth mentioning that the test group ICG/DOX-loaded NHTPNs 1501 and the test group ICG/DOX-loaded TPNs 1503 do show having the effect of temperature elevation in the tumor, and the highest temperatures are 60.2° C. and 56.3° C. respectively. In addition, the test group ICG/DOX-loaded TPNs 1502 had the highest temperature of 50.3° C. in the tumor. The above results obtained by using the IVIS system detection also report that, the NHTPNs carrier used to deliver the ICG can indeed effectively accumulate the ICG in the tumor, and the expression of photo-triggered hyperthermia effect was superior so as to inhibit the tumor growth. As is evident from FIG. 15, the test group free ICG 1504 under the identical conditions, due to it not being accumulated in the tumor by not being able to effectively use the EPR effect, and also the test group free ICG 1504 being cleared away quickly during the blood circulation, the photothermal local warming effect was inferior and the highest temperature was only at 41.4° C.

Figure 16:
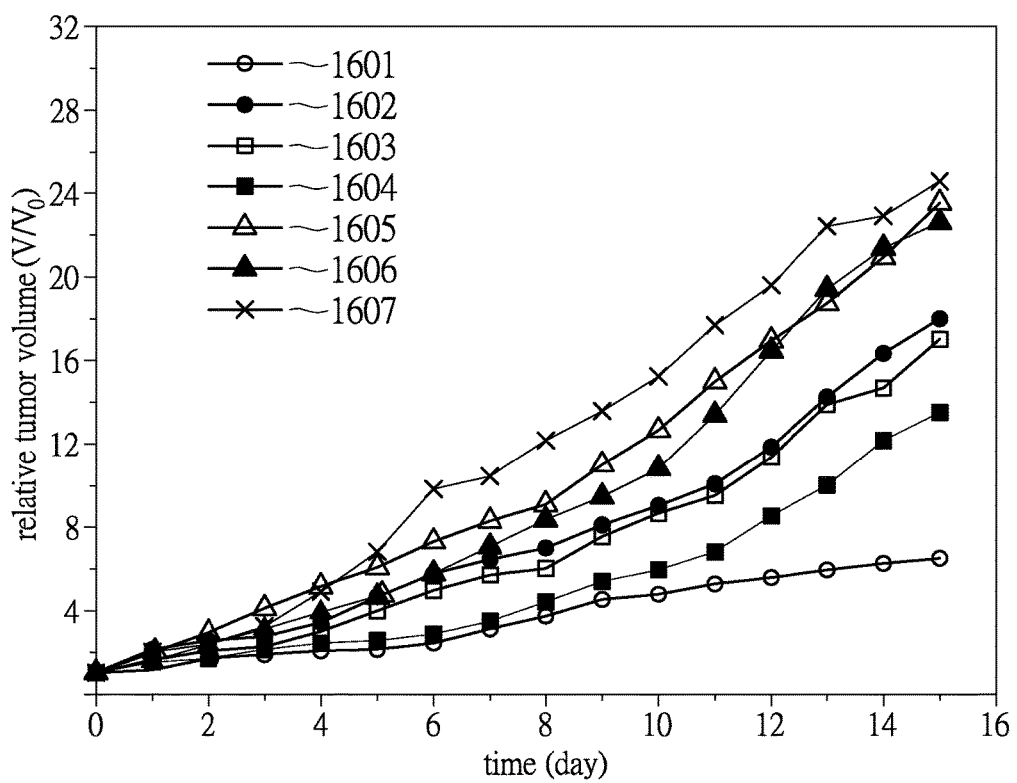
FIG. 16 is a time—tumor volume figure of the pH-responsive nanoparticle ICG/DOX-loaded NHTPNs of an embodiment in the instant disclosure.

FIG. 16 is a time—tumor volume figure of the pH-responsive ICG/DOX-loaded NHTPNs of the embodiment in the instant disclosure. In order to observe the tumor inhibition effect, after NIR laser irradiation, the tumor volume and the mouse weight were monitored lasting 15 days after administration. The tumor volume result and the tumor volume at first (day 0) of each group were standardized respectively, and a trend of relative tumor volume having changed over time was obtained.

The results show that, a test group PBS+laser 1607, a test group Free ICG+laser 1605, and a test group Free DOX+laser 1606 were subjected to the NIR laser irradiation that had no significant tumor growth inhibition effect, originating from free DOX and free ICG could not be effectively accumulated in the tumor, the tumor growth could not be inhibited through chemotherapy or light triggered thermal generation, and the relative mouse tumor volume was increased about 22 to 26 times.

In contrast, a test group ICG/DOX-loaded NHTPNs+laser 1601 and test group ICG-loaded NHTPNs+laser 1604 expressed the similar effect of tumor growth inhibition in the 1 to 7 days of treatment. It is worth noting that, in the 8 to 15 days of treatment, comparing to the test group ICG/DOX-loaded NHTPNs+laser 1601, the test group ICG-loaded NHTPNs+laser 1604 mouse has more significant incidence of tumor relapse.

The abovementioned results show that, the test group ICG-loaded NHTPNs+laser 1604 effectively accumulated in the tumor and was irradiated by the NIR laser, and high heat was generated to cause lethal thermal injury for the tumor cancer cells in the early phase of treatment. However, single administration and illumination generated photothermal therapy cannot comprehensively kill the cancer cells so as to bring about subsequent tumor relapse.

It is worth mentioning that, for the test group ICG/DOX-loaded NHTPNs+laser 1601, due to the strong photothermal therapy in the treatment of the early phase with subsequent chemotherapy. The PLGA core of pH-responsive ICG/DOX-loaded NHTPNs was continuously degraded to promote DOX release, so as to effectively inhibit the cancer cell proliferation and achieve the superior effect of tumor growth inhibition. Additionally, the experiment found that, if the test group ICG/DOX-loaded NHTPNs 1602 was not subjected to the NIR laser, that is, only relying on the DOX chemotherapy, the effect of tumor inhibition was far inferior than the test group ICG/DOX-loaded NHTPNs+laser 1601.

Third Embodiment

The pH-responsive nanoparticle of another embodiment of the instant disclosure was that, firstly, the DOX.HCl was dissolved in DMSO and excess triethylamine (1.5-fold excess in molar concentration with respect to DOX) was then added therein to stir for 24 hours at room temperature in the dark, and the purpose was to increase a hydrophobicity of the DOX, so as to improve the drug loading efficiency. The ideal condition was that the triethyl amine was added in an amount of 4 times the molar concentration of the DOX.

The DMSO solution containing 1.8 mg NAcHis-TPGS was dripped and dispersed into the 0.01 M phosphate buffer (pH 7.4) under stirring with a magnet, and was then stirred for 5 minutes with rotating speed of 1350 rpm. The ideal condition was that the 0.05 mL DMSO solution containing 1.8 mg NAcHis-TPGS (feed amount is 80 wt % of the PLGA) was dripped into the 2.8 mL phosphate buffer.

Then, the DMSO solution containing PLGA (LA/GA=85/15 mol ratio), DOX, and nano metal particles superparamagnetic iron oxide Nanoparticles (SPION) was slowly dripped into the NAcHis-TPGS contained phosphate buffer solution (DMSO/Water (v/v)=1/7) to stir for 30 minutes at 30° C. with the magnet in the dark. The ideal condition was that the 350 µL DMSO solution contains 2 mg PLGA, 0.4 mg DOX, and 0.2 mg SPION therein. Furthermore, the nano metal particles are only one kind of developing agents, and it is not limited herein.

The abovementioned solution was put into the dialysis bag (MWCO 12000 to 14000), and the phosphate buffer (pH 7.4, 0.01M) was dialyzed for 24 hours to remove the unloaded drugs and DMSO, so as to obtain a pH-responsive SPION/DOX-loaded NHTPNs solution, and the purified pH-responsive nanoparticle solution was stored in a 4° C. refrigerator for subsequent experiments.

Fourth Embodiment

The N-acetyl Histidine was used to modify 1,2-distearoyl-sn-glycero-3-phosphoethanolamine-N-[maleimide(polyethylene glycol (DSPE-PEG) to synthesize NAcHis-DSPE-PEG by Steglich esterification.

DSPE-PEG, N-acetyl-1-histidine, DCC, and a bit of DMAP were dissolved in 10 mL DMSO, followed by stirring the above mixed solution for 48 hours at 40° C. The ideal condition was that, the N-acetyl-1-histidine was added in an amount of 5 times the molar number of the DSPE-PEG, and the DCC was added in an amount of 8 times the molar number of the DSPE-PEG.

The DCU was removed by suction filtration, and the product was placed in the dialysis bag (MWCO 1000), followed by dialysis against DMSO for 7 days to remove the residual reactants, and then dialysis against the deionized water for 7 days to remove DMSO. Finally, the solution was frozen and dried to obtain a product called NAcHis-DSPE-PEG.

The DOX.HCl was dissolved in DMSO and triethyl amine was then added therein to stir for 48 hours at room temperature in the dark, a salt form DOX was reduced to base form to increase the hydrophobicity so as to improve the drug loading efficiency. The ideal condition was that the triethyl amine was added in an amount of 2 times the molar number of the DOX.

The premodified NAcHis-DSPE-PEG was dissolved in DMSO and phosphate buffer (pH 7.4) was then dripped therein to vigorously stir for 5 minutes, and the 2.0 mg PLGA (LA/GA=85/15 molar ratio) and 0.4 mg DOX predissolved in DMSO were slowly dripped therein and then vigorously stirred for 30 minutes.

The above evenly mixed solution was stood for 30 minutes at room temperature and was then put into the dialysis bag (MWCO 12000 to 14000), and then dialyzed against the phosphate buffer for one day at 4° C. to remove the unloaded DOX and DMSO. The DOX-loaded NAcHis-DSPE-PEG/PLGA Nanoparticles is abbreviated to DOX-loaded NHDPNs.

Fifth Embodiment

The preparation method of NAcHis-DSPE-PEG was identical to <Fourth Embodiment>, so it does not bear repeating here. The DOX.HCl was dissolved in DMSO and excess triethylamine (1.5-fold excess in molar concentration with respect to DOX) was added therein to stir for 24 hours at room temperature in the dark, the purpose was to increase the hydrophobicity of the DOX, so as to improve the drug loading efficiency. The ideal condition was that the triethyl amine was added in the amount of 2 times the molar concentration of the DOX.

The DMSO solution containing NAcHis-DSPE-PEG was dripped and dispersed into the 0.01 M phosphate buffer (pH 7.4), and was then stirred for 5 minutes with rotating speed of 1350 rpm. The DMSO solution containing PLGA (LA/GA=85/15 mol ratio), DOX, and ICG was slowly dripped into the phosphate buffer solution containing NAcHis-DSPE-PEG (DMSO/Water (v/v)=1/7) and stirred at 30° C. for 30 minutes in the dark. The ideal condition was that, 2.0 mg PLGA, 0.4 mg DOX, and 0.4 mg ICG, and 0.35 mL DMSO.

The abovementioned solution was put into the dialysis bag (MWCO 12000 to 14000), and dialyzed against the phosphate buffer (pH 7.4, 0.01M) for 24 hours to remove the unloaded drugs and DMSO, so as to obtained a pH-responsive ICG/DOX-loaded NAcHis-DSPE-PEG/PLGA nanoparticles (referred as ICG/DOX-loaded NHDPNs) solution, and the dialyzed pH-responsive nanoparticle solution was stored in the 4° C. refrigerator.

Sixth Embodiment

The preparation method of NAcHis-DSPE-PEG was identical to <Fourth Embodiment>, so it does not bear repeating here. The pH-responsive nanoparticle of another embodiment of the instant disclosure was that, first, the DOX.HCl was dissolved in DMSO and excess triethylamine (1.5-fold excess in molar concentration with respect to DOX) was then added therein to stir for 24 hours at room temperature in the dark, and the purpose was to increase the hydrophobicity of the DOX, so as to improve the drug loading efficiency. The ideal condition was that the triethyl amine was added in an amount of 2 times the molar concentration of the DOX.

The NAcHis-DSPE-PEG contained DMSO solution was dripped and dispersed into the 0.01 M phosphate buffer (pH 7.4) under stirring with the magnet, and was then stirred for 5 minutes with rotating speed of 1350 rpm. The DMSO solution containing PLGA (LA/GA=85/15 mol ratio), DOX, and SPION was slowly dripped into the phosphate buffer solution containing NAcHis-DSPE-PEG (DMSO/Water (v/v)=1/7) to stir for 30 minutes at 30° C. with the magnet in the dark. The ideal condition was that, 2.0 mg PLGA, 0.4 mg DOX, and 0.2 mg SPION, and 0.35 mL DMSO.

Then, the abovementioned solution was put into the dialysis bag (MWCO 12000 to 14000), and then dialyzed against the phosphate buffer (pH 7.4, 0.01M) for 24 hours to remove the unloaded drugs and DMSO, so as to obtain a pH-responsive SPION/DOX-loaded NHDPNs solution, and the dialyzed pH-responsive nanoparticle solution was stored in the 4° C. refrigerator.

The descriptions illustrated supra set forth simply the preferred embodiments of the present invention; however, the characteristics of the present invention are by no means restricted thereto. All changes, alterations, or modifications conveniently considered by those skilled in the art are deemed to be encompassed within the scope of the present invention delineated by the following claims.

What is claimed is:

1. A pH-responsive nanoparticle made of a pH-responsive polymer and a poly(lactic-co-glycolic acid) by self-assembly,
   wherein the pH-responsive polymer is formed by a polyethylene glycol derivative and a R-Histidine derivative through a chemical reaction;
   wherein the surface electric potential of the pH-responsive nanoparticle is −25 to 10 mV, such that when a pH value of the pH-responsive nanoparticle is changed from 7.4 to 5.0 depending upon an external environment, a surface zeta potential of the pH-responsive nanoparticles is converted from negative charge to positive charge;
   wherein the pH-responsive polymer is connected to poly(lactic-co-glycolic acid) through the polyethylene glycol derivative;
   wherein the pH-responsive nanoparticle includes a structure as: PLGA-PEG-H in which H represents only one residue of a monomer of the R-Histidine derivative selected from a group consisting of N-acetyl-Histidine, L-Histidine, D-Histidine and 3-Methyl-L-histidine.

2. The pH-responsive nanoparticle as claimed in claim 1, wherein the pH-responsive polymer is formed from the conjugation of the polyethylene glycol derivative and the R-Histidine derivative via an esterification.

3. The pH-responsive nanoparticle as claimed in claim 2, wherein the polyethylene glycol derivative is Vitamin E TPGS or DSPE-PEG.

4. The pH-responsive nanoparticle as claimed in claim 1, wherein the pH-responsive nanoparticle includes a hydrophilic shell and a hydrophobic core, and the hydrophilic shell is located at an outer side of the hydrophobic core.

5. The pH-responsive nanoparticle as claimed in claim 4, wherein the hydrophobic core further lade an anticancer drug, developer, photothermal agent, nano-metal particle, or combinations thereof.

6. A pH-responsive nanoparticle adapted for preparation of a delivery system capable of promoting the tumor accumulation of anticancer drug and an application of a deep tumor penetration of drug, comprising:
   (a) a polyethylene glycol derivative and a R-Histidine derivative subjected to a chemical reaction to form a pH-responsive polymer; and
   (b) the pH-responsive polymer and a poly(lactic-co-glycolic acid) underwent a self-assembly process to form the pH-responsive nanoparticles, wherein a surface zeta potential of the pH-responsive nanoparticles under different pH conditions is −25 to 10 mV;
   wherein the pH-responsive polymer is connected to poly(lactic-co-glycolic acid) through the polyethylene glycol derivative;
   wherein the pH-responsive nanoparticle includes a structure as: PLGA-PEG-H in which H represents only one residue of a monomer of the R-Histidine derivative selected from a group consisting of N-acetyl-Histidine, L-Histidine, D-Histidine and 3-Methyl-L-histidine.

7. The pH-responsive nanoparticle adapted for preparation of a delivery system capable of promoting the tumor accumulation of anticancer drug and an application of a deep tumor penetration of drug, as claimed in claim 6, wherein the polyethylene glycol derivative is Vitamin E TPGS or DSPE-PEG.

8. The pH-responsive nanoparticle adapted for preparation of a delivery system capable of promoting the tumor accumulation of anticancer drug and an application of a deep tumor penetration of drug, as claimed in claim 6, wherein the pH-responsive nanoparticle includes a hydrophilic shell and a hydrophobic core, and the hydrophilic shell is located at an outer side of the hydrophobic core.

9. The pH-responsive nanoparticle adapted for preparation of a delivery system capable of promoting the tumor accumulation of anticancer drug and an application of a deep tumor penetration of drug, as claimed in claim 8, wherein the hydrophobic core further loads an anticancer drug, developer, photothermal agent, nano-metal particle, or combinations thereof.

10. A pH-responsive nanoparticle made of a pH-responsive polymer and a poly(lactic-co-glycolic acid) by self-assembly, comprising a chemical structure as follow:

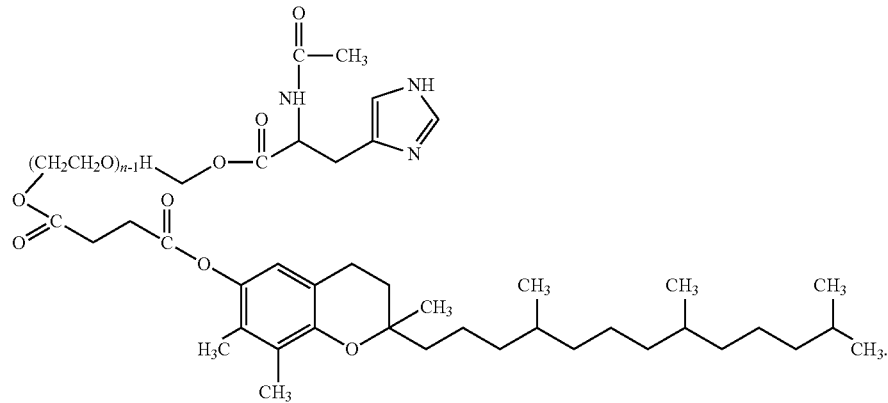

* * * * *